United States Patent [19]

Smith

[11] 4,171,441
[45] Oct. 16, 1979

[54] PREPARATION OF QUINAZOLIN-2(1H)-ONES

[75] Inventor: Joseph A. Smith, Fanwood, N.J.

[73] Assignee: Sandoz, Inc., E. Hanover, N.J.

[21] Appl. No.: 926,928

[22] Filed: Jul. 21, 1978

Related U.S. Application Data

[63] Continuation-in-part of Ser. No. 830,411, Sep. 6, 1977, abandoned.

[51] Int. Cl.$^2$ .......................................... C07D 239/82
[52] U.S. Cl. ................................................. 544/286
[58] Field of Search ............................... 544/284, 286

[56] References Cited

U.S. PATENT DOCUMENTS

| | | |
|---|---|---|
| 3,563,990 | 2/1971 | Hardtmann .......................... 260/251 |
| 3,937,705 | 2/1976 | Hardtmann .................. 260/251 QB |

*Primary Examiner*—Raymond V. Rush
*Attorney, Agent, or Firm*—Gerald D. Sharkin; Richard E. Vila

[57] ABSTRACT

Quinazoline-2(1H)-ones are prepared by dehydrogenating a 5,6,7,8-tetrahydro-2(1H)-quinazolinone with sulfur in the presence of a metal oxide, hydroxide or halide.

18 Claims, No Drawings

PREPARATION OF QUINAZOLIN-2(1H)-ONES

This is a continuation-in-part of application Ser. No. 830,411, filed Sept. 6, 1977, now abandoned.

It is known that quinazolin-2(1H)-ones can be prepared by dehydrogenating a corresponding 5,6,7,8-tetrahydro-2(1H)-quinazolinone with sulfur. Such process, however, results generally in low yields due in large part to the formation of a 3,4-dihydro-quinazolin-2(1H)-one by-product.

The principal object of the present invention is to provide an improved process for the preparation of quinazolin-2(1H)-ones by dehydrogenation of 5,6,7,8-tetra-2(1H)-quinazolinones, particularly a process in which the amount of 3,4-dihydro-quinazolin-2(1H)-one by-product is substantially reduced, and especially a process in which such by-product formation is reduced and desired yield substantially enhanced.

The objectives of this invention are accomplished to obtain quinazolin-2(1H)-ones of the formula I:

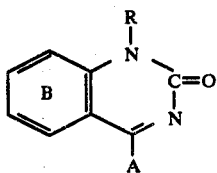

wherein R is an optionally mono, di- or tri-halo substituted hydrocarbon of 1 to 8 carbon atoms, A is monocyclic aryl and Ring B is optionally mono- or di-substituted by alkyl of 1 to 3 carbon atoms, by dehydrogenating a corresponding 5,6,7,8-tetrahydro-2(1H)-quinazolinone of the formula II:

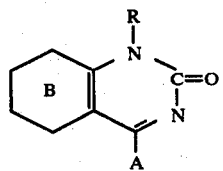

wherein R, A and Ring B are as above defined, with sulfur in an inert organic solvent and in the presence of a metal oxide, hydroxide or halide which forms a metal sulfide under the reaction conditions.

The process of the invention may be effected at temperatures in the range of from 125° C. to 250° C., preferably 130° C. to 200° C., and more preferably in the range of 135° C. to 170° C. The reaction is carried out in an organic solvent for said compound II and sulfur at the reaction temperature, which solvent may be any of several conventional organic liquids providing an inert solvent medium. Examples of such solvents include ethylene glycol, propylene glycol, ethoxyethoxyethanol, dioxane, toluene, xylene and p-cymene. It is generally preferred to employ a solvent boiling at the desired reaction temperature in order to utilize reflux conditions, e.g., p-cymene or xylene under the more preferred temperature conditions.

The amount of sulfur employed may vary fairly widely. At least about 1.7 mols of sulfur per mol of the compound II are required for the better results and the higher yields made possible by the process of the invention. The upper limit on the amount of sulfur is not particularly critical. As a practical matter, it is unnecessary and inefficient to employ the sulfur in an amount exceeding a mol ratio to the compound II of 6:1. More suitably, the mol ratio of sulfur to the compound II will be in the range of from 1.9:1 to 4:1, preferably in the range of 2:1 to 3:1.

The metal oxide, hydroxide or salt to be used in the invention may be essentially any inorganic oxide, hydroxide or salt of a metal other than the alkali metals and those of Periods II and III (magnesium and aluminum) of the Periodic Table of Elements. As a practical matter, the rare earth metals (atomic numbers 57–71) and the metals with atomic number of 84 or greater are less suitable. Examples of metals which may be specifically mentioned are calcium, titanium, zirconium, chromium, lead, molybedenum, manganese, iron, tin, cobalt, nickel, palladium, copper, silver, zinc, cadmium, mercury, antimony and bismuth. The generally preferred metals are calcium, iron and zinc. The metal salts, when employed, are preferably salts of strong acids such as the chloride, sulfate and nitrate (and, of course, other than a sulfide). In general, the preferred compounds are the oxides and the hydroxides, particularly the oxides, eg. calcium oxide, zinc oxide and iron oxide, especially zinc and ferric oxide, particularly ferric oxide. A number of the metal compounds which may be employed, eg. calcium chloride, react with hydrogen sulfide to produce metal sulfides which tend to be unstable or soluble under the reaction conditions and which further react with release of hydrogen sulfide. In such cases it is particularly preferred to include in the reaction mixture a hydroxide base such as an alkali metal hydroxide or alkaline earth metal hydroxide, or to use an excess of a hydroxide base when such a base is itself employed as the metal compound. The hydroxide base employed in such situations is preferably an alkali metal hydroxide, eg. potassium hydroxide or sodium hydroxide. It will be appreciated that metal salts tend to form acidic mediums on reaction with hydrogen sulfide and that the certain metal sulfides tend to be unstable or soluble in such acidic media. It is for these reasons that a hydroxide base will be more commonly used when a metal salt is used and that the metal oxides and metal hydroxides, particularly the oxides, are generally preferred. It will of course further be evident that the more preferred metal compounds are those forming, or ultimately forming, a stable metal sulfide under the reaction conditions. Nevertheless, very good results can be obtained with a metal salt and hydroxide base as hereinafter specifically exemplified by the use of calcium chloride and sodium hydroxide.

The amount of the metal oxide, hydroxide or salt to be employed is generally determined relative to the amount of the compound II, and is not critical with even small amounts being indicated to be beneficial. However, in general, at least about 1.0 mole, more usually at least 1.5 mols, of the metal oxide, hydroxide or salt are required for the better results. The upper limit on the amount of metal compound is not important and controlled essentially by practical considerations such that mol ratios of the metal compound to compound II in excess of 10:1 offer no additional advantage and tend to be wasteful. The mol ratios of the preferred metal oxides to compound II are more usually in the range of from 1.8:1 to 6:1, preferably 2:1 to 4:1 and more preferably in the range of from 2.1:1 to 3:1. Varying amounts of hydroxide base may be employed when sulfides tending to be unstable or soluble are formed, but in general it is desirable to employ at least 1.0 mole, more usually at least 1.5 mols, per mol of the compound II, preferably 1.8 to 6 mols per mol of compound II, more preferably 2 to 3 mols per mol of the compound II. Reaction time is typically of the order of 1 to 15 hours.

The metal sulfide formed during the reaction results from the reaction of the metal oxide, hydroxide or salt or ionized or reduced form thereof with hydrogen sulfide and such reaction is apparently sufficiently rapid that undesired side reactions are suppressed or essentially eliminated.

The process of the present invention may be carried out at subatmospheric or superatmospheric pressure conditions, but is most suitably effected at about atmospheric pressure. A blanket or constant flow of an inert gas, e.g., nitrogen, over the reaction mixture is desirable and preferred, but not essential. The process readily provides good yields of the order of at least 50%, most usually at least 60%, with yields of at least 65% generally obtainable under preferred conditions.

The compounds II are either known per se or may be prepared from known materials by procedures described in the literature.

In the compounds of the formulae I and II, the substituent R is typically alkyl of 1 to 6 carbon atoms, cycloalkyl of 3 to 7 carbon atoms, cycloalkylalkyl of 4 to 7 carbon atoms in which the cycloalkyl portion is of 3 to 6 carbon atoms and the alkyl portion is of 1 or 2 carbon atoms, phenyl, benzyl or phenethyl. Typical examples of halo substituted hydrocarbons are represented by mono-, di- and tri-halo substituted alkyl of 1 to 6 carbon atoms in which the halo is fluoro, chloro or bromo, and mono- or di-halo substituted phenyl, benzyl or phenethyl in which the halo is fluoro, chloro or bromo. Such di- or tri-halo substituted hydrocarbons are preferably substituted by the same halogen atoms, e.g., trichloro-substituted propyl.

Typical examples of A in the compounds of the formulae I and II are optionally mono- or di-substituted phenyl in which the substituents are one or two from the group consisting of halo (fluoro, chloro or bromo), alkyl of 1 to 3 carbon atoms or alkoxy of 1 to 3 carbon atoms or one tri-fluoromethyl substituent, and optionally monosubstituted 2-thienyl in which the optional substituent is halo (fluoro, chloro or bromo), alkyl of 1 to 3 carbon atoms or alkoxy of 1 to 3 carbon atoms.

Compounds of the formula I are, for example, known for their anti-inflammatory activity in animals and in this regard R is preferably alkyl of 1 to 6 carbon atoms or cyclopropylmethyl, more preferably alkyl of 1 to 6 carbon atoms, especially isopropyl, A is phenyl or substituted phenyl as above specifically delineated, especially phenyl or p-fluorophenyl, and Ring B is unsubstituted but most preferably alkyl, especially methyl, substituted once or twice, more particularly with at least one such alkyl, especially methyl, substituent being in the 7-position. The process of the invention is judged to be particularly advantageous in providing an efficient synthetic route for such preferred anti-inflammatory substances herein indicated, but generally operating independently of the significance of R, A and Ring B as hereinbefore first set forth.

The following examples illustrate the process of the invention.

EXAMPLE 1

A mixture of 200 ml. of p-cymene, 40 g. of ferric oxide and 7 g. of sulfur is heated to reflux (ca. 175° C.), and there is then added thereto dropwise over a period of 40 minutes a hot (130° C.) solution of 28.2 g. of 7-methyl-1-isopropyl-4-phenyl-5,6,7,8-tetrahydro-2(1H)-quinazolinone in 200 mls. of p-cymene. The resulting solution is refluxed for 3.5 hours during which time 1.8 mls. of water are collected in a Dean Stark separator. The reaction solution is then cooled to 28° C. and filtered through a celite pad which is then washed 4 times each with 25 mls. of toluene. The toluene washings are extracted with 50 mls. of 4 N. hydrochloric acid and the p-cymene filtrate is extracted with 350 mls. of 4 N. hydrochloric acid. The acid extracts are combined and extracted with 100 mls. of toluene, and such toluene extracts discarded. The acid solution remaining after such toluene extraction is treated by addition of 350 mls. of toluene and 100 g. of 50% aqueous sodium hydroxide solution. The phases are separated and the toluene phase washed twice each with 100 mls. of water, followed by drying over sodium sulfate, filtering and evaporation in vacuo. The solid residue is crystallized from ethyl acetate to obtain 7-methyl-1-isopropyl-4-phenyl-quinazolin-2(1H)-one, m.p. 139°–141° C.

EXAMPLE 2

Following the procedure of Example 1, there are similarly prepared:
(A) 5,7-dimethyl-1-isopropyl-4-phenyl-quinazolin-2(1H)-one.
(B) 1-isopropyl-7-methyl-4-(p-methylphenyl)-quinazolin-2(1H)-one.
(C) 1-isopropyl-7-methyl-4-(p-fluorophenyl)-quinazolin-2(1H)-one.
(D) 1-isopropyl-7-methyl-4-(2-thienyl)-quinazolin-2(1H)-one.

EXAMPLE 3

A mixture of 28.2 g. of 7-methyl-1-isopropyl-4-phenyl-5,6,7,8-tetrahydro-2(1H) quinazolinone, 9.6 g. of sulfur, 10 gms of sodium hydroxide, 20 gms of calcium chloride and 200 mls of carbitol (2-[2-ethoxyethoxy]ethanol) is heated under a nitrogen blanket at 150° C. for 2 hours. The resulting mixture is then cooled to 65° C., 500 mls. of benzene added and the mixture cooled with stirring to 15° C. and the liquid phase decanted. The organic phase is washed with water and evaporated to obtain an oil which is dissolved in a mixture of 100 mls of benzene and 100 mls of 50% aqueous hydrochloric acid. The resulting mixture is stirred for one hour at room temperature, the phases separated and the acid phase treated with 50 mls of benzene. The acid phase is neutralized with 50% sodium hydroxide solution, extracted with 150 mls of benzene and the benzene extracts washed with water until neutral. After drying over sodium sulfate, the benzene solution is evaporated to obtain the crude product which is recrystallized from ethylacetate to obtain 1-isopropyl-4-phenyl-7-methyl-2[1H]quinazolinone, m.p. 141°–142° C.

EXAMPLE 4

To a stirred mixture of 4.3 g. of sulfur, 6.8 g. of zinc oxide and 67 ml. of a mixture of xylenes heated to reflux (ca. 138° C.) under a nitrogen blanket is added a preheated (100°–115° C.) solution of 10.0 g. of 7-methyl-1-isopropyl-4-(p-fluorophenyl)-5,6,7,8-tetrahydro-2(1H)-quinazolinone in 100 ml. of a mixture of xylenes. After addition (ca. 20 minutes), the resulting mixture is refluxed overnight, cooled and filtered through celite. The solids are washed with toluene and the filtrate and washings extracted four times with 4 N. hydrochloric acid and the extracts washed with 100 ml. of toluene. The aqueous phase is treated with 200 ml. of toluene and treated portionwise with 115 g. of 50% sodium hydroxide solution in an ice bath. The aqueous phase is extracted twice each with 100 ml. of toluene and the organic phase water washed and dried. The crude yellow solid obtained on filtering and concentration in vacuo is dissolved in 100 ml. of ethyl acetate, filtered, concentrated to a volume of 50 ml. and cooled to 0° C. to obtain a precipitate which is recrystallized from ethyl acetate to 7-methyl-1-isopropyl-4-(p-fluorophenyl)-quinazolin-2(1H)-one, m.p. 175°–176.5° C.

EXAMPLE 5

The procedure of Example 4 is repeated employing an equivalent molar amount of lead dioxide in place of zinc oxide whereby a yield improvement but of a lesser order of magnitude is obtained employing more extensive recovery procedures.

EXAMPLE 6

A mixture of 2.5 g sulphur, 13.3 g of ferric oxide and 67 mls of xylene, is heated under reflux under a nitrogen blanket, in a flask fitted with a Dean Stark H₂O collector. To this mixture is added dropwise over a period of 20 minutes a hot solution (100° C.–110° C.) of 10 gms 7-methyl-1-isopropyl-4-p-fluorophenyl-5,6,7,8-tetrahydro-2-(1H)quinazolinone in 100 mls of xylene. After heating at reflux for 10 hours after the addition, the mixture is cooled to 80° C. and filtered through celite. Wash the flask residue and filter cake successively, three times, using 50 mls of toluene each time. The filtrates are combined, then extracted successively with 200, 100, and then 50 mls of 4 N Hydrochloric acid. The acid extracts are combined and washed with 100 mls of toluene. Separate and discard the organic phases. To the acid mixture is added 200 mls of toluene, and then with stirring and cooling neutralized with 115 g of 50% aq. NaOH. The phases are separated and the aqueous phase extracted twice using 100 mls of toluene each time. The combined toluene phases are washed twice using 100 mls of water each time. The mixture is dried over anhydrous magnesium sulphate, filtered through celite, then concentrated to yellow crystals of 1-isopropyl-4-p-fluorophenyl-7-methyl-2(1H)quinazolinone, which is recrystallized from ethylacetate to obtain the analytic sample, mp 175°–176.5° C.

What is claimed is:

1. In the process for preparing a compound of the formula:

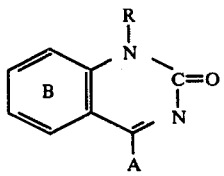

wherein R is an optionally mono, di- or tri- halo substituted hydrocarbon of 1 to 8 carbon atoms in which the halo is fluoro, chloro or bromo, A is phenyl optionally mono- or di-substituted independently by fluoro, chloro, bromo, alkyl of 1 to 3 carbon atoms or alkoxy of 1 to 3 carbon atoms or monosubstituted by trifluoromethyl or A is 2-thienyl optionally monosubstituted by fluoro, chloro, bromo, alkyl of 1 to 3 carbon atoms or alkoxy of 1 to 3 carbon atoms and Ring B is optionally mono- or di-substituted by alkyl of 1 to 3 carbon atoms, by dehydrogenating a corresponding 5,6,7,8-tetrahydro-2(1H)-quinazolinone of the formula:

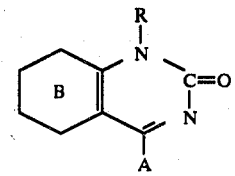

wherein R, A and Ring B are as above defined, with sulfur in an inert organic solvent; the improvement comprising carrying out such dehydrogenation in the presence of an inorganic metal compound which is an oxide, hydroxide or salt and which forms a metal sulfide under the reaction conditions, the metal in said metal compound being other than magnesium, aluminum and an alkali metal.

2. The process of claim 1 in which the metal compound is a metal oxide.

3. The process of claim 1 in which the metal in the metal compound is calcium, iron or zinc.

4. The process of claim 3 in which the metal compound is ferric oxide or zinc oxide.

5. The process of claim 4 in which the metal compound is ferric oxide.

6. The process of claim 1 in which the mol ratio of metal compound to said tetrahydro-2(1H)-quinazolinone is at least 1:1.

7. The process of claim 4 in which the mol ratio of metal compound to said tetrahydro-2(1H)-quinazolinone is at least 1.5:1.

8. The process of claim 7 in which the dehydrogenation is carried out at a temperature of from 125° C. to 250° C., and in which the mol ratio of sulfur to said tetrahydro-2(1H)-quinazolinone is at least 1.7:1.

9. The process of claim 8 in which the temperature is in the range of from 130° C. to 200° C.; in which the mol ratio of sulfur to said tetrahydro-2(1H)-quinazolinone is in the range of 1.9:1 to 4:1, and in which the mol ratio of the metal compound to said tetrahydro-2(1H)-quinazolinone is 2:1 to 4:1.

10. The process of claim 9 in which R is alkyl of 1 to 6 carbon atoms or cyclopropylmethyl and A is phenyl optionally mono- or di-substituted independently by fluoro, chloro, bromo, alkyl of 1 to 3 carbon atoms or alkoxy of 1 to 3 carbon atoms or monosubstituted by trifluoromethyl.

11. The process of claim 5 in which R is alkyl of 1 to 6 carbon atoms and A is phenyl optionally mono- or di-substituted independently by fluoro, chloro, bromo, alkyl of 1 to 3 carbon atoms or alkoxy of 1 to 3 carbon atoms or mono-substituted by trifluoromethyl.

12. The process of claim 9 in which R is isopropyl, A is phenyl or p-fluorophenyl and Ring B bears a methyl substituent of the 7-position.

13. The process of claim 12 in which Ring B bears a 7-methyl substituent as the only Ring B substituent.

14. The process of claim 13 in which A is phenyl.

15. The process of claim 13 in which A is p-fluorophenyl.

16. The process of claim 1 in which R is alkyl of 1 to 6 carbon atoms, cycloalkyl of 3 to 7 carbon atoms, cycloalkylalkyl of 4 to 7 total carbon atoms in which the cycloalkyl portion is of 3 to 6 carbon atoms and the alkyl portion of 1 or 2 carbon atoms, phenyl, benzyl, phenethyl, alkyl of 1 to 6 carbon atoms mono-, di- or tri-substituted independently by fluoro, chloro or bromo or phenyl, benzyl or phenethyl mono- or di-substituted independently by fluoro, chloro or bromo, and in which A is phenyl optionally mono-or di-substituted independently by fluoro, chloro, bromo, alkyl of 1 to 3 carbon atoms or alkoxy of 1 to 3 carbon atoms or mono-substituted by trifluoromethyl or 2-thienyl optionally monosubstituted by fluoro, chloro, bromo, alkyl of 1 to 3 carbon atoms or alkoxy of 1 to 3 carbon atoms.

17. The process of claim 13 in which the metal compound is ferric oxide in a mol ratio to said tetrahydro-2(1H)-quinazolinone of 2:1 to 3:1.

18. The process of claim 3 in which the metal compound is calcium chloride in a mol ratio to said tetrahydro-2(1H)-quinazolinone of at least 1:1 and in which the reaction is additionally carried out in the presence of sodium hydroxide or potassium hydroxide in a mole ratio to said tetrahydro-2(1H)-quinazolinone of at least 1:1.

* * * * *